(12) United States Patent
Setbacken et al.

(10) Patent No.: US 8,493,064 B2
(45) Date of Patent: Jul. 23, 2013

(54) APPARATUS, SYSTEM, AND METHOD FOR MAINTAINING NORMALCY OF A SENSOR WITH RESPECT TO A STRUCTURE

(75) Inventors: Mike Setbacken, Pasco, WA (US);
Mark Gehlen, Pasco, WA (US); Steve Hubbard, Pasco, WA (US); Fred Perrin, Pasco, WA (US)

(73) Assignee: United Western Technologies Corporation, Kennewick, WA (US)

( * ) Notice: Subject to any disclaimer, the term of this patent is extended or adjusted under 35 U.S.C. 154(b) by 512 days.

(21) Appl. No.: 12/862,645

(22) Filed: Aug. 24, 2010

(65) Prior Publication Data
US 2012/0049842 A1 Mar. 1, 2012

(51) Int. Cl.
*G01N 27/82* (2006.01)
*G01R 33/12* (2006.01)

(52) U.S. Cl.
USPC ............ 324/237; 324/238; 324/240; 324/239

(58) Field of Classification Search
None
See application file for complete search history.

(56) References Cited

U.S. PATENT DOCUMENTS

| | | | |
|---|---|---|---|
| 4,219,774 A * | 8/1980 | Rogel et al. | 324/262 |
| 4,271,393 A | 6/1981 | Hansen et al. | |
| 4,622,517 A | 11/1986 | Arnaud et al. | |
| 4,677,379 A | 6/1987 | Arnaud et al. | |
| 4,814,705 A | 3/1989 | Saunderson | |
| 5,298,858 A * | 3/1994 | Harrison | 324/235 |
| 5,485,084 A | 1/1996 | Duncan et al. | |
| 5,510,709 A | 4/1996 | Hurley et al. | |
| 5,781,007 A * | 7/1998 | Partika et al. | 324/220 |
| 6,014,024 A | 1/2000 | Hockey et al. | |
| 6,271,664 B1 | 8/2001 | Logue | |
| 6,636,037 B1 | 10/2003 | Ou-Yang | |
| 6,894,492 B1 * | 5/2005 | Dziech | 324/238 |
| 7,155,307 B2 * | 12/2006 | Seemann | 700/245 |
| 7,352,176 B1 | 4/2008 | Roach et al. | |
| 7,375,514 B2 | 5/2008 | Rempt et al. | |
| 7,542,871 B2 * | 6/2009 | Rempt et al. | 702/168 |
| 7,560,920 B1 | 7/2009 | Ouyang et al. | |
| 7,626,383 B1 | 12/2009 | Sun et al. | |
| 2003/0164700 A1 | 9/2003 | Goldfine et al. | |
| 2004/0257072 A1 * | 12/2004 | Samson | 324/242 |
| 2005/0200355 A1 * | 9/2005 | Hatcher et al. | 324/239 |
| 2009/0302835 A1 | 12/2009 | Sun et al. | |
| 2010/0013468 A1 | 1/2010 | Joubert et al. | |
| 2010/0045276 A1 | 2/2010 | Udpa et al. | |
| 2011/0124269 A1 * | 5/2011 | Tada et al. | 451/5 |
| 2011/0260721 A1 * | 10/2011 | Fischer | 324/229 |

FOREIGN PATENT DOCUMENTS

EP 1798550 A1 6/2007

* cited by examiner

*Primary Examiner* — Jay Patidar
(74) *Attorney, Agent, or Firm* — Goucher Patent Law, PLLC; Tyler Goucher

(57) ABSTRACT

An apparatus, system, and method are disclosed for scanning metallic surfaces. The apparatus, in one embodiment, comprises a shaft and a rotating member. The rotating member may comprise a sensing end and a featuring engaging element. The shaft further comprises a first coupling element and the rotating member further comprises a second coupling element. The first coupling element may be coupleable with the second coupling element such that the rotating member is pivotable at any three-dimensional angle with respect to the shaft to orient the sensing surface parallel to the scanned surface.

20 Claims, 13 Drawing Sheets

APPARATUS, SYSTEM, AND METHOD FOR MAINTAINING NORMALCY OF A SENSOR WITH RESPECT TO A STRUCTURE

FIELD OF THE INVENTION

This subject matter of the present disclosure relates to scanning surfaces and more particularly relates to scanning the metallic surfaces of aircraft.

BACKGROUND

Aircraft require a high level of maintenance and care to assure their safe use. Most aircraft comprise a metallic fuselage that is held together by metallic rivets. Both the fuselage and the rivets may occasionally require scanning to determine if weaknesses have developed within the metal.

In some circumstances, it is beneficial to be able to scan the fuselage of the aircraft without having to remove the rivets or disassemble the aircraft. Further, in some circumstances it is beneficial to be able to scan the surface of the fuselage immediately surrounding a feature, such as a rivet, without having to scan the feature itself.

Difficulties may arise in attempting to scan around a feature and still maintain a sensor sufficiently close to the surface to be scanned. Another difficulty may be keeping the sensor parallel to the surface that is being scanned while scanning around a feature.

SUMMARY

From the foregoing discussion, it should be apparent that a need exists for an improved apparatus, system, and method for scanning the surface of an aircraft. Beneficially, such an apparatus, system, and method would allow for efficient scanning of an aircraft surface while taking into account various features of the surface such as rivets.

The subject matter of the present disclosure has been developed in response to the present state of the art, and in particular, in response to the problems and needs in the art that have not yet been fully solved by currently available technology. Accordingly, the present subject matter has been developed to provide a portable inspection system, and associated apparatus and method, for the inspection of aircraft structures that overcome many or all of the above-discussed shortcomings in the art.

An apparatus is disclosed for scanning surfaces, which may be metallic surfaces in some embodiments. The apparatus, in one embodiment, includes a shaft and a rotating member. The rotating member may include a sensing end and a featuring engaging element. The shaft further includes a first coupling element and the rotating member further includes a second coupling element. The first coupling element and the second coupling element may be coupled together such that the shaft may pivot at any three-dimensional angle with respect to the rotating member while a sensing surface of the sensing end remains parallel to a scanned surface.

In some embodiments, the first coupling element may include one of a ball and a socket and the second coupling element may include the other of the ball and the socket. When coupled together, the first coupling element and the second coupling element may define a ball-and-socket joint.

In further embodiments, a third coupling element may include one of a pin and a slot and a fourth coupling element may include the other of the pin and the slot. When the pin and the slot are coupled they may facilitate co-rotation of the shaft and the rotating member.

In certain embodiments, the sensing surface may be in coupled to the sensing end. A magnetic-field-inducing element may also be coupled to the sensing end. The sensing surface and the magnetic-field-inducing element may be positioned within a sensor module. In some embodiments the sensing surface and the magnetic-field-inducing element may be positioned within or on a feature engaging element that engages a feature on the scanned surface.

The rotating member, in certain embodiments, may be in coupled to the sensing end by a threaded connection. In one embodiment, the threaded connection may facilitate manufacturing of the device. In other embodiments, the threaded connection may allow the sensing end to be detachable from the rotating member such that different sensing ends with different feature engaging elements may be attached to the apparatus.

In one embodiment, the feature engaging element may include a fastener receiving cavity adapted to engage a feature, such as a head of a rivet. In other embodiments, the feature engaging element may be adapted to engage a bolt, a screw, a hole, a chamfer of a hole, or any other feature that may be located on a metallic surface.

In some embodiments, the feature engaging element may include a geometric shape adapted to align a central axis of the feature engaging element with a central axis of a hole when the feature engaging element is inserted into the hole. In some embodiments, the apparatus may include a aligning element that is engageable with a hole and adapted to align a central longitudinal axis of the hole with a central longitudinal axis of the rotating member.

A method of the present disclosure is also presented for scanning a surface. In certain embodiments, the method substantially includes the steps necessary to carry out the functions presented above with respect to the operation of the described apparatus and system. In one embodiment, the method includes providing an apparatus for scanning a surface. The apparatus includes a user engaging portion, a feature engaging element, and a sensing surface. The feature engaging element is engaged with a feature disposed on a surface such that the sensing surface is parallel to a scanned surface. A magnetic field is induced in the scanned surface and the sensing surface senses a reaction to the induced magnetic field.

In certain embodiments, the feature engaging element is pivotable to any three-dimensional angle with respect to the user engaging portion. In one embodiment, the sensing surface is maintained parallel to the scanned surface irrespective of the orientation of the user engaging portion with respect to the scanned surface.

The method, in one embodiment, may also include providing a shaft having a first coupling element and providing a rotating member having a second coupling element, the feature engaging element, and a sensing end. The first coupling element is coupled with the second coupling element such that the rotating member is pivotable at any three-dimensional angle with respect to the shaft to orient the sensing surface parallel to the scanned surface.

In a further embodiment, the method includes coupling the first coupling element with the second coupling element such that the shaft and the rotating member co-rotate. In such an embodiment, the rotating member may be rotated by rotating the shaft.

Reference throughout this specification to features, advantages, or similar language does not imply that all of the features and advantages that may be realized with the subject matter of the present disclosure should be or are in any single embodiment. Rather, language referring to the features and advantages is understood to mean that a specific feature, advantage, or characteristic described in connection with an embodiment is included in at least one embodiment. Thus, discussion of the features and advantages, and similar language, throughout this specification may, but do not necessarily, refer to the same embodiment.

Furthermore, the described features, advantages, and characteristics of the subject matter may be combined in any suitable manner in one or more embodiments. One skilled in the relevant art will recognize that the subject matter may be practiced without one or more of the specific features or advantages of a particular embodiment. In other instances, additional features and advantages may be recognized in certain embodiments that may not be present in all embodiments.

These features and advantages of the present subject matter will become more fully apparent from the following description and appended claims, or may be learned by the practice of the subject matter as set forth hereinafter.

BRIEF DESCRIPTION OF THE DRAWINGS

In order that the advantages of the subject matter of the present disclosure will be readily understood, a more particular description of the subject matter briefly described above will be rendered by reference to specific embodiments that are illustrated in the appended drawings. Understanding that these drawings depict only typical embodiments and are not therefore to be considered to be limiting of its scope, the subject matter will be described and explained with additional specificity and detail through the use of the accompanying drawings, in which.

DETAILED DESCRIPTION

Figure 1:
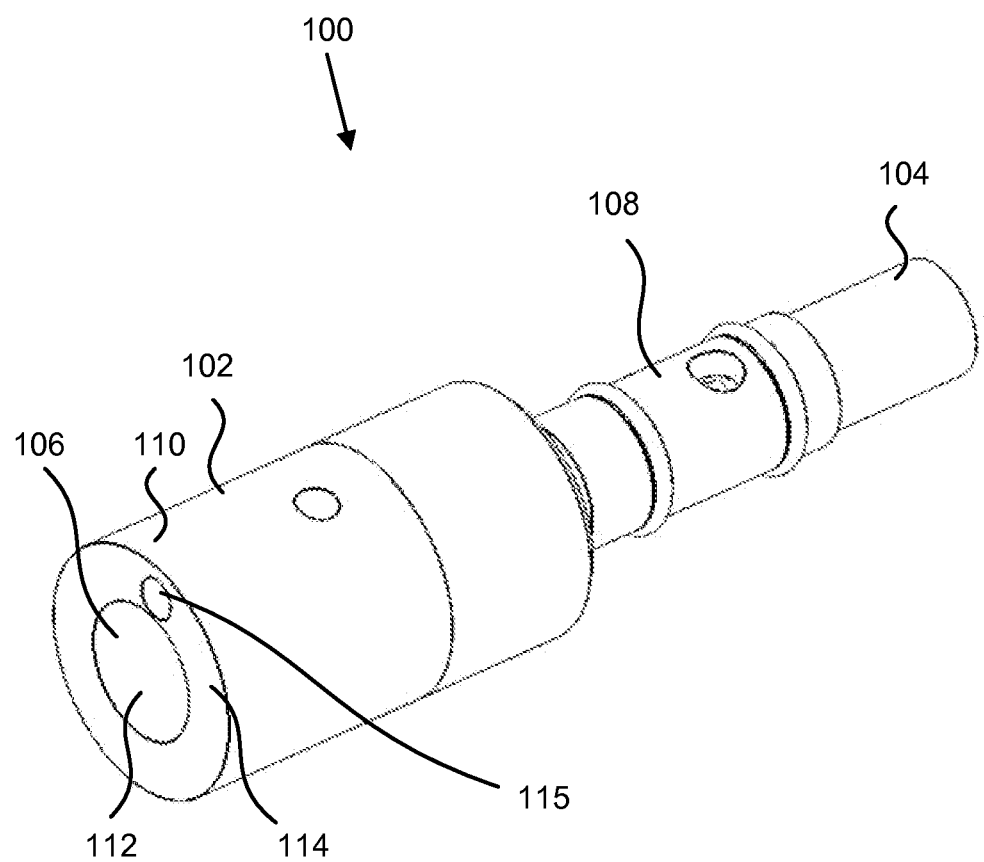
FIG. 1 is a perspective view illustrating one embodiment of an apparatus for maintaining a sensing surface parallel to a scanned surface.

Reference throughout this specification to "one embodiment," "an embodiment," or similar language means that a particular feature, structure, or characteristic described in connection with the embodiment is included in at least one embodiment of the present disclosure. Thus, appearances of the phrases "in one embodiment," "in an embodiment," and similar language throughout this specification may, but do not necessarily, all refer to the same embodiment.

Furthermore, the described features, structures, or characteristics of the subject matter may be combined in any suitable manner in one or more embodiments. In the following description, numerous specific details are provided, such as examples of programming, software modules, user selections, network transactions, database queries, database structures, hardware modules, hardware circuits, hardware chips, etc., to provide a thorough understanding of embodiments of the subject matter. One skilled in the relevant art will recognize, however, that the subject matter may be practiced without one or more of the specific details, or with other methods, components, materials, and so forth. In other instances, well-known structures, materials, or operations are not shown or described in detail to avoid obscuring aspects of the subject matter.

The schematic flow chart diagrams included herein are generally set forth as logical flow chart diagrams. As such, the depicted order and labeled steps are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

The present disclosure relates to the field of scanning apparatuses and scanning methods that utilize eddy currents to scan metallic surfaces for weaknesses and deformities. A major industry for such scanning technology is the aeronautical industry. Aircraft require a high level of maintenance and care to assure its safe use.

An eddy current scanning apparatus comprises at least one generating coil through which a current runs. The generating coil is held in proximity to the metallic surface that is to be scanned. A current is generated through the generating coil such that the generating coil induces an electromagnetic field. The magnetic field may then penetrate the metallic surface. Eddy currents may form if the metallic surface is moved through the generated magnetic field or if the magnetic field is changing. In some embodiments, the eddy currents may be generated by running an AC current through the coil and placing the coil proximate to the metallic surface. In other embodiments, the eddy currents may be generated by running a DC current through the coil and then moving either the coil or the metallic surface.

Variations in the electrical conductivity or the magnetic permeability of the metallic surface may cause the eddy currents to vary in phase and magnitude. These variations in conductivity and permeability may be caused by weaknesses or abnormalities in the metallic surface. The eddy currents will generate their own electromagnetic field, which may in turn induce a current on the generating coil. The induced current may also vary in phase and magnitude due to variations in the conductivity and permeability of the metallic surface. The generating coil may be used to measure changes in the generated eddy currents by measuring any changes in the current running through the coil caused by the current that is induced in the coil by the eddy currents. In other embodiments, a second coil may be used to measure the eddy currents.

Changes in the amplitude and phase of the current may be interpreted into information about the metallic surface. Some of the gathered information may include, but is not limited to, detection of cracks, measurement of the thickness of a material, identification of the type of material, and identification of abnormalities in the material composition.

Most aircraft structures include a metallic fuselage that is held in place by metallic rivets. An apparatus and method for using eddy currents to scan for weaknesses is well suited for use on an aircraft because the surface can be scanned without requiring the removal of all the rivets and disassembly of the aircraft. In some circumstances, it is desirable to scan the surface of the aircraft surrounding a feature, such as a rivet, without scanning that actual feature itself. In other circumstance it may be desirable to scan the interior of a rivet hole after the rivet has been removed.

Each of the above circumstances presents unique challenges. For example, when scanning a surface, maintaining an eddy current sensor parallel to a surface being scanned may be difficult. This difficulty may be caused by the scanned surface being disposed at a difficult angle, the scanned surface including a feature, such as a rivet or a rivet hole, or the scanned surface being in a location that is difficult to reach. In some embodiments, the present apparatus, and associated systems and methods, may aid in maintaining a sensing surface parallel to a scanned surface while the scanned surface is being scanned.

As shown in FIG. 1, one embodiment of an apparatus 100 to maintain a sensing surface parallel to a scanned surface includes a shaft 104 coupled to a rotating member 102. The shaft 104 includes a driving tool coupling point 108 adapted to co-rotationally couple the shaft 104 to a driving tool (not shown). In other words, the driving tool is configured to drive or rotate the shaft 104, which in turn is configured to rotate the rotating member 102. In one embodiment, the driving tool may provide a current to the apparatus 100 such that the apparatus 100 is able to induce magnetic fields into a scanned surface. The driving tool may also actuate the apparatus 100 by rotating the shaft 104 via the driving tool coupling point 108. In certain embodiments, the magnetic field is induced by an AC current running through a sensor module 115. In other embodiments, the magnetic field is induced by a DC current running through the sensor module 115. In DC embodiments, rotation of shaft 104 and rotating member 102 causes the DC current to pass over the scanned surface to create a changing magnetic field which in turn induces eddy currents. Cracks or imperfections in the scanned surface produce a change in the eddy currents which inturn produce a voltage output that can be detected by the sensor module 115. In AC embodiments, when an alternating current is applied to a conductor, such as a copper wire, a magnetic field develops in and around the conductor which induces small currents in the scanned surface. Due to the changing electrical field in AC embodiments an alternating current does not need to be passed over the scanned surface, rather the alternating current itself induces the eddy currents. As with the DC embodiments, cracks or imperfections in the scanned surface produce a change in the eddy currents which inturn produce a voltage output that can be detected by the sensor module 115.

The rotating member 102 includes a sensing end portion 110 that is distal from the shaft 104. The sensing end portion 110 has an end surface defined as a sensing surface 114. In certain implementations, the sensing surface 114 is substantially perpendicular to a central axis of the rotating member 102. Additionally, the rotating member 102 includes a feature engaging element 106 positioned at the sensing end 110. As shown, in some implementations, the feature engaging element 106 is formed in the sensing surface 114. For example, the feature engaging element 106 includes a fastener receiving cavity 112 adapted to receive the head of a fastener, such as a rivet, bolt head, nut, or the like. In some embodiments, the sensing surface 114 and the magnetic-field-inducing element may comprise a single coil. In other embodiments, the magnetic-field-inducing element may include a first coil and the sensing surface 114 may include a second coil. In one embodiment the magnetic-field-inducing element may be a conductor, such as a copper wire, coupled to an electrical source to deliver an alternating current or direct current to the conductor.

The rotating member 102 also includes a sensor module 115 positioned on the sensing end portion 110, and in some instances, on the sensing surface 114. The sensor module 115, in one embodiment, senses changes in eddy currents and provides feedback to a user. In certain embodiments, the feedback may be interpreted by a processing unit (not shown). The interpreted feedback may then be displayed by a display unit (not shown) such as an LCD terminal or other display device known in the art. In one embodiment, the interpreted feedback may be displayed as a two-dimensional or three-dimensional representation of the scanned surface 600 or structure.

When scanning a surface with the apparatus 100, the driving mechanism is attached to the shaft 104 and the feature engaging element 106 is engaged with a feature, such as a rivet, on a scanned surface. The driving mechanism may rotate the shaft 104 causing the rotating member 102 to co-rotate with the shaft 104 (i.e., rotate at the same rotational velocity). Rotating the rotating member 102 rotates the sensing surface 114 around the rivet with the sensor module 115 scanning the scanned surface around the rivet without scanning the rivet itself. In other embodiments the rivet may also be scanned. In some implementations, the shaft 104 may be rotated at a rate as low as 0.1 RPM to as high as 5,000 RPM. In other implementations, the shaft may be rotated at a rate of 1,500 RPM.

Figure 2:
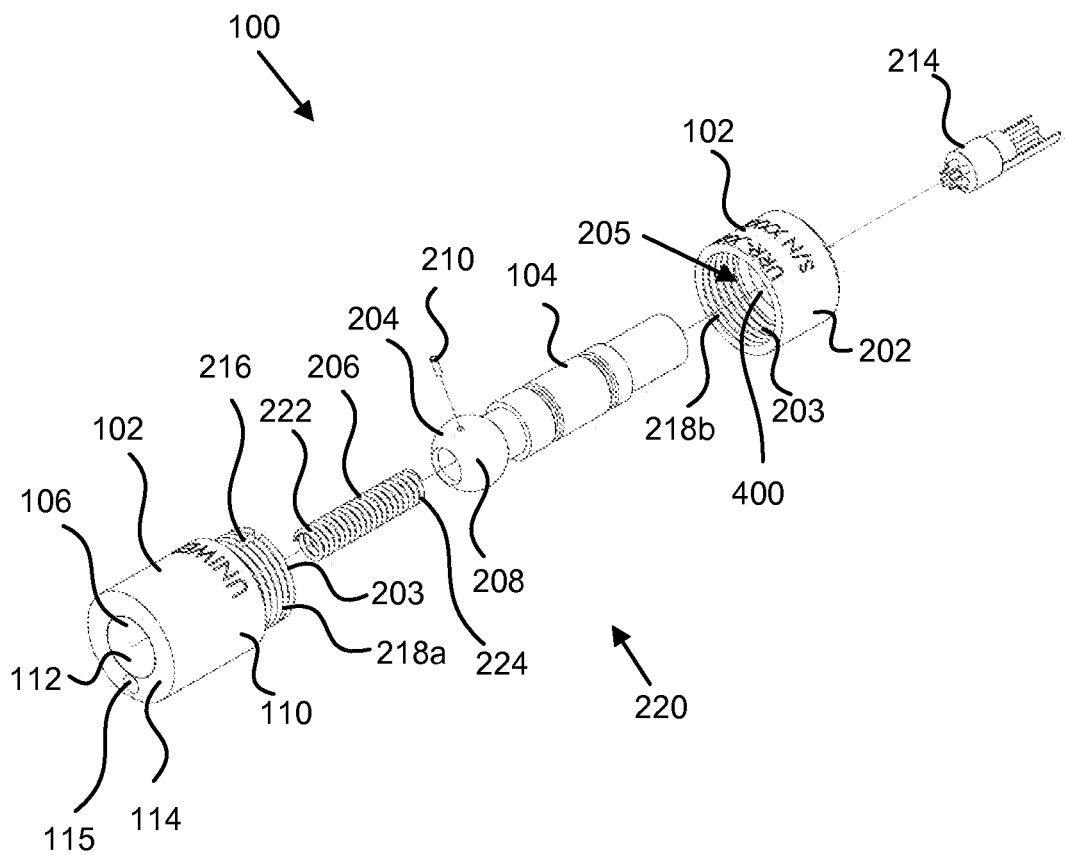
FIG. 2 is an exploded perspective view illustrating another embodiment of an apparatus for maintaining a sensing surface parallel to a scanned surface.

FIG. 2 depicts an exploded view of an embodiment of the apparatus 100. Other embodiments of the apparatus 100 may include fewer features than depicted, while still further embodiments of the apparatus may include additional features and components that are not depicted in FIG. 2.

As shown, the rotating member 102 includes an attachment end portion 202 and a sensing end portion 110. The sensing end portion 110 and the attachment end portion 202 may be attached to each via any of various coupling techniques. For example, as shown, the sensing end portion 110 includes external threads 218a and the attachment end portion 202 includes internal threads 218*b* threadably engageable with the external threads to couple the sensing end portion 110 and attachment end portion 202 together. In certain other implementations, the sensing end portion 110 can include the internal threads 218*b* and the attachment end portion 202 can include the external threads 218*a*. The depiction of a threaded connection is meant to be illustrative and not limiting. Accordingly, in other embodiments, the sensing end portion 110 and attachment end portion 202 can be coupled together via a slot and groove attachment, a press fit, a brazed joint, a welded joint, or other similar coupling techniques. In one embodiment, the coupling portion may operate to assist in manufacturing the apparatus 100. In such an embodiment, each element of the apparatus 100 may be separately molded and then combined to create the apparatus 100.

In some embodiments, the coupling portion 218 facilitates interchanging the sensing end portion 110 of the rotating member 102 with one or more other sensing end portions (not shown).

In certain embodiments, the sensing end portion 110 and the other sensing end portions both include feature engaging elements that are each engageable with a different feature on a scanned surface. For example, as described in more detail below, in certain embodiments, the feature engaging elements may each include one of a fastener receiving cavity, a nub (see, e.g., nub 704 of FIG. 7), a spherical element (see, e.g., spherical element 902 of FIG. 9), and a cylinder (see, e.g., cylinder 1000 of FIG. 10). To promote ease in changing between different sensing end portions to engage a different feature on a scanned surface, the coupling portion 218 may be configured to facilitate interchangeability between the different sensing end portions and the attachment end portion 202. In other embodiments, the coupling portion 218 may allow a user to disassemble a portion of the apparatus 100 in the field to provide maintenance to the apparatus or to change some other portion of the apparatus. Although some embodiments of the apparatus include interchangeable sensing ends for engaging different surface features, in other embodiments, separate apparatuses with non-interchangeable sensing ends may be provided for each type of surface feature that may be encountered.

Referring again to FIG. 2, the shaft 104 includes a first coupling element 204 having an at least partly spherical or ball portion 208. The rotating member 102 includes a second coupling element 203 (e.g., socket) that matingly receives and retains the spherical portion 208. The sensing end 110 and the attachment end 202 include respective portions of the second coupling element 203. When coupled together, the respective portions of the sensing and attachment ends 110, 202 form the second coupling element 203. The second coupling element 203 defines an at least partially spherical socket 205 with a diameter approximately equal to the diameter of the spherical portion 208. The socket 205 includes an opening (see opening 400 of FIG. 4) that has a diameter that is large enough for a portion of the shaft 104 to pass through but small enough to prevent passage of the spherical portion 208. The spherical portion 208 is retained within the socket 205 of the second coupling element 203 by placing the spherical portion between the sensing end 110 and the attachment end 202, and securing the sensing and attachment ends 110, 202 together to form the socket 205. When coupled together, the spherical portion 208 and the socket 205 form a ball-and-socket joint 220 between the shaft 104 and the rotating member 102. Accordingly, the coupling between the first coupling element 204 and the second coupling element 203 facilitates pivoting of the rotating member 203 in any three-dimensional angle with respect to the shaft 104 to orient the sensing surface 114 parallel to a scanned surface.

In certain embodiments, the ball-and-socket joint 220 allows the shaft 104 to be pivotable to any three-dimensional angle within a conical space. Therefore, the ball-and-socket joint 220 allows a user to pivot the shaft 104 to an angle with respect to a scanned surface and still orient the sensing surface 114 parallel to the scanned surface.

In addition to the first and second coupling elements 204, 203, the apparatus includes a third coupling element 210 and a fourth coupling element 216. The third and fourth coupling elements 210, 216 are engageable to facilitate co-rotation of the shaft 104 and the rotating member 102. In the embodiment illustrated in FIG. 2, the third coupling element 210 is a pin coupled to the shaft 104 and the fourth coupling element 216 is a slot disposed on the sensing end 110 of the rotating member 102. The pin 210 is receivable by the slot 216 to prevent relative rotation (i.e., to facilitate co-rotation) between the rotating member 201 and the shaft 104.

Although the embodiment illustrated in FIG. 2 depicts the third coupling member 210 (e.g., pin) as being coupled to the second coupling element 204 (e.g., an external surface of the spherical portion 208) and the fourth coupling element 216 (e.g., slot) as being disposed in the sensing end portion of the rotating member 102, one of skill in the art will recognize in view of this disclosure that location of the pin and slot may be reversed. For example, in certain embodiments, the pin 210 may be coupled to the rotating member 102 and the slot 216 may be located on the first coupling element 204. Additionally, in some embodiments, the slot 216 may be positioned in the attachment end portion 202 of the rotating member 102. While the embodiment illustrated in FIG. 2 depicts the third coupling element 210 as being a pin, in other embodiments the third coupling element 210 may comprise a bolt, a protrusion, or some other feature extending from the apparatus 100. Also, in other embodiments, the fourth coupling element 216 may include a ridge, a catch, or some other feature adapted to allow the third coupling element 210 to freely travel along a vertical axis of the apparatus 100, but prevent the third coupling element 210 from traveling perpendicular with respect to the fourth coupling element 216.

Figure 3:
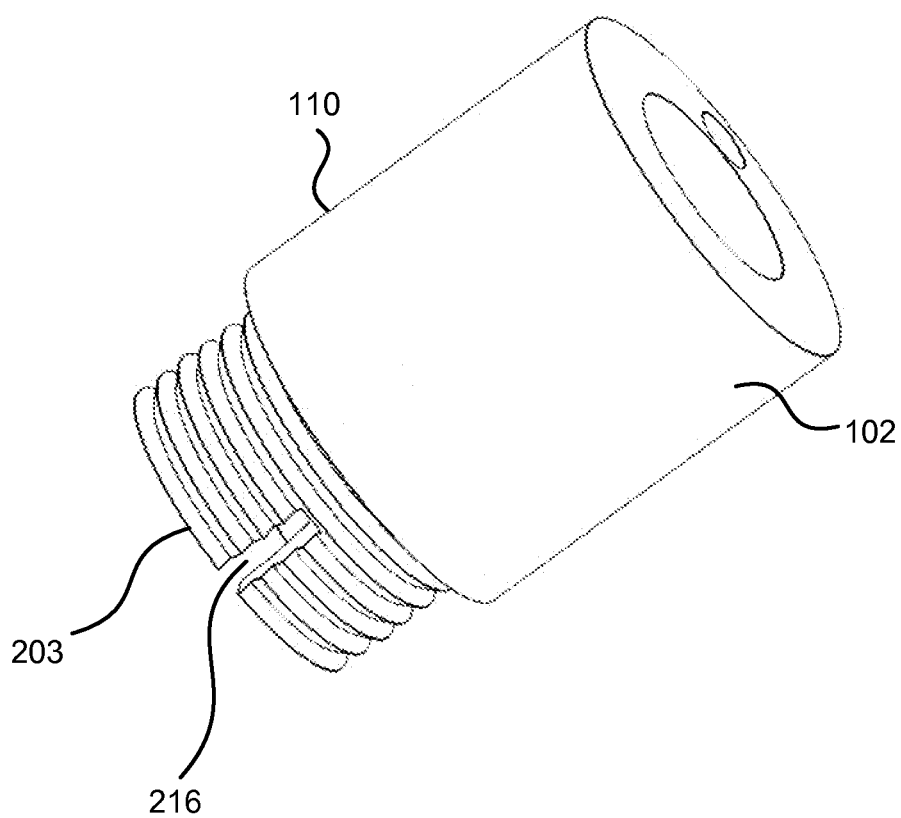
FIG. 3 is a perspective view illustrating one embodiment of a sensing end of an apparatus for maintaining a sensing surface parallel to a scanned surface.

Referring to FIG. 3, the slot 216 is formed in the sensing end portion 110 of the rotating member 102. In certain embodiments, the slot 216 extends lengthwise parallel to a longitudinal axis of the sensing end portion 110. The slot 216 allows the pin 210 to travel along the length of the slot while substantially preventing the pin from traveling perpendicular to the length of the slot. Substantially preventing the pin 210 from traveling perpendicular to the slot 216 facilitates co-rotation between the rotating member 102 and the shaft 104 such that a rotational force applied to the shaft 104 is equally applied to the rotating member 102. In other embodiments, the slot 216 may be disposed on the attachment end 202 of the rotating member 102 and operate in a substantially similar manner. The slot 216 and pin 210 rotationally couple the rotating member 102 to the shaft 104 such that rotating the shaft 104 will also cause the rotating member 102 to rotate irrespective of the angle of the shaft 104 with respect to the rotating member 102. In certain embodiments, the slot may be positioned on the ball 208 and the pin may be positioned within the socket 205. Similarly, in another embodiment the ball may be integral with the rotating member 102 and the socket may be included in the shaft 104. In such an embodiment the pin and slot may be located on either the rotating member 102 or the shaft.

Referring back to FIG. 2, in certain embodiments, the apparatus 100 may also include a biasing member 206. In the illustrated embodiment, the biasing member 206 is a spring. However, in other embodiments, the biasing member 206 may be a rubber element, a chamber of compressed fluid, or some other element that would exert a biasing force that biases the rotating member 102 into a coaxial relationship with the shaft 104. The biasing member 206 includes a first end 222 and a second end 224. The first end 222 of the biasing member 206 may be coupled to the rotating member 102 and the second end 224 of the biasing member 206 may be coupled to the shaft 104. When assembled, the biasing member 206 may exert a force to at least one of the rotating member 102 and the shaft 104 to align the rotating member 102 in a coaxial orientation with the shaft 104. In other words, without an external force acting on the apparatus 100, the biasing force from the biasing member 206 biases the rotating member 102 into coaxial alignment with the shaft 104.

The apparatus 100 may further include an electronic module 214 for inducing magnetic fields and/or receiving information, such as information regarding eddy currents, from the sensor module 115. The electronic module 214 may be replaceable with a variety of different electronic modules that each provide different magnetic field inducing qualities or different data gathering abilities. The electronic module 214 can be powered by an external power supply and/or an onboard battery. The electronic module 214 may be in communication with a processing unit (not shown) that is adapted to both interpret the information received from the sensing surface 114 and to generate appropriate magnetic field inducing currents. The processing unit may include an oscilloscope, a computer, a microcontroller, or any other processing unit that is known in the art. The processing unit may store the information to be processed at a later time or may process the information in real time. In one embodiment the apparatus may include a display unit (not shown) such as an LCD terminal or other display device known in the art that displays the information processed by the processing unit.

Figure 4:
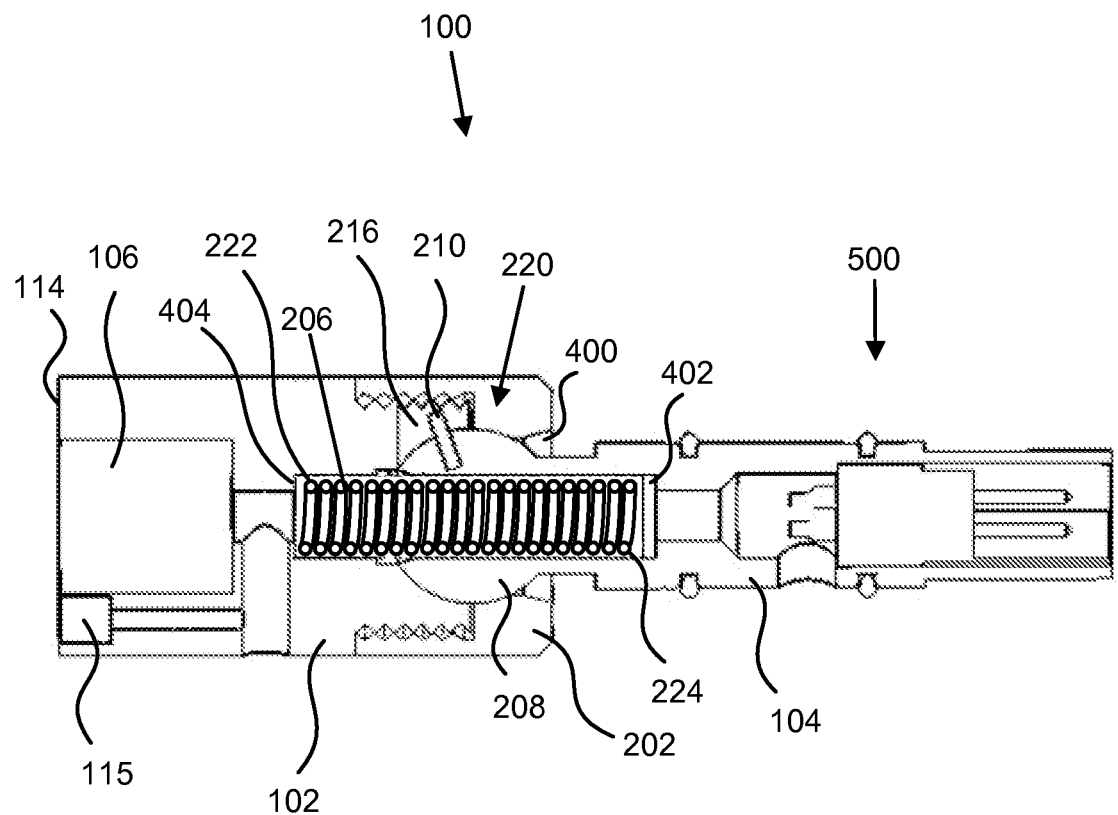
FIG. 4 is a cross-sectional view illustrating one embodiment of an apparatus for maintaining a sensing surface parallel to a scanned surface.

Referring to FIG. 4, the shaft 104 may include an internal shaft recess 402, and the rotating member 102 may include an internal rotating member recess 404. The first end 222 of the biasing member 206 may be seated within the internal rotating member recess 404 and the second end 224 of the biasing member 206 may be seated within an internal shaft recess 402. As discussed above, in certain embodiments, the biasing member 206 may exert a biasing force between the rotating member 102 and the shaft 104 such that the rotating member 102 becomes coaxial with the shaft 104 when there is no other external force operating of the rotating member 102. In certain embodiments, the biasing force may be sufficient to align the shaft 104 and the rotating member 102 in a coaxial orientation when no external force is applied to the shaft 104 or rotating member 102 but may yield to an external force applied to either the shaft 104 or rotating member 102 to align the sensing surface 114 parallel to a scanned surface 600.

Figure 5:
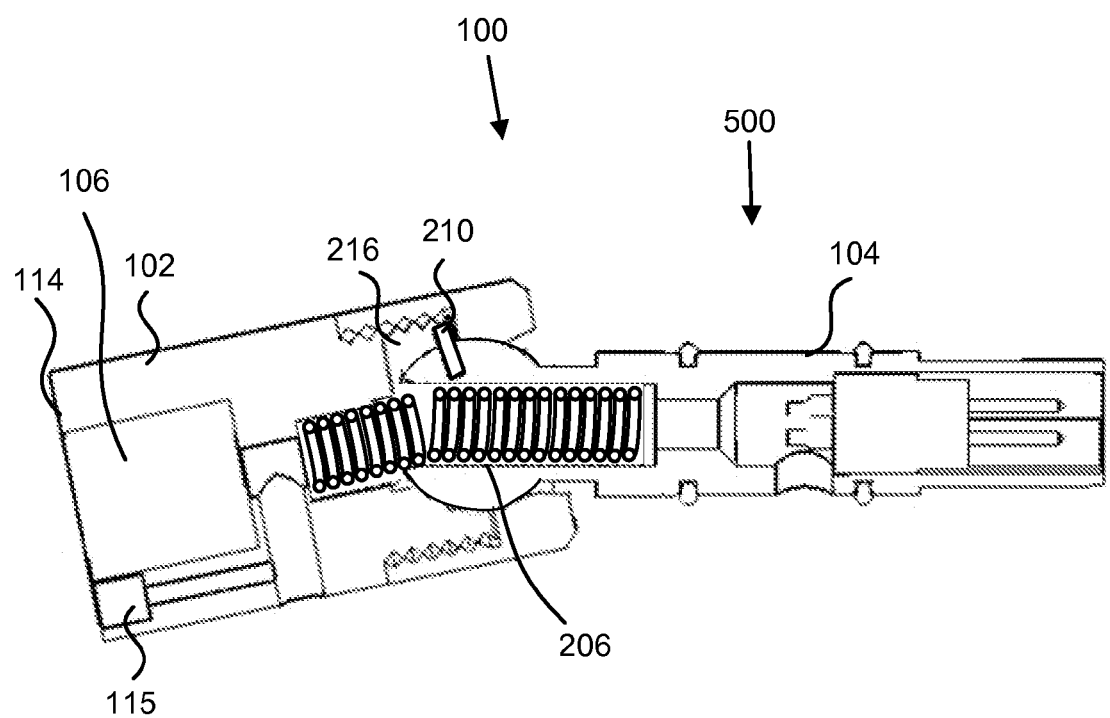
FIG. 5 is a cross-sectional view illustrating the apparatus of FIG. 4 with a rotating member in a non-coaxial orientation with respect to a shaft.

As shown in FIG. 5, the rotating member 102 is pivoted out of a coaxial relationship with respect to the shaft 104. Accordingly, the pin 210 has traveled a longitudinal distance along the slot 216. The biasing member 206 has also been displaced to allow the rotating member 102 to be tilted out of coaxial alignment with respect to the shaft 104. When the force that is causing the rotating member 102 to pivot with respect to the shaft 104 is released, the biasing member 206 may exert a force on the rotating member 102 and the shaft 104 that causes the rotating member 102 to straighten with respect to the shaft 104 as depicted in FIG. 4.

In certain embodiments the apparatus 100 may comprise a user engaging portion 500. The user engaging portion 500 may be adapted to be held by a user while scanning a scanned surface. In some embodiments, the user engaging portion 500 may comprise the shaft 104. In other embodiments, the user engaging portion 500 may comprise a driving tool (not shown) that is attached to the shaft 104. When used for scanning a surface, such as the surface of an aircraft, the apparatus 100 allows the user engaging portion 500 to be pivotable into an infinite number of three-dimensional angles with respect to the feature engaging element 106. This allows the sensing surface 114 to remain parallel to a scanned surface while the user engaging portion or shaft is moved or reoriented.

Figure 6:
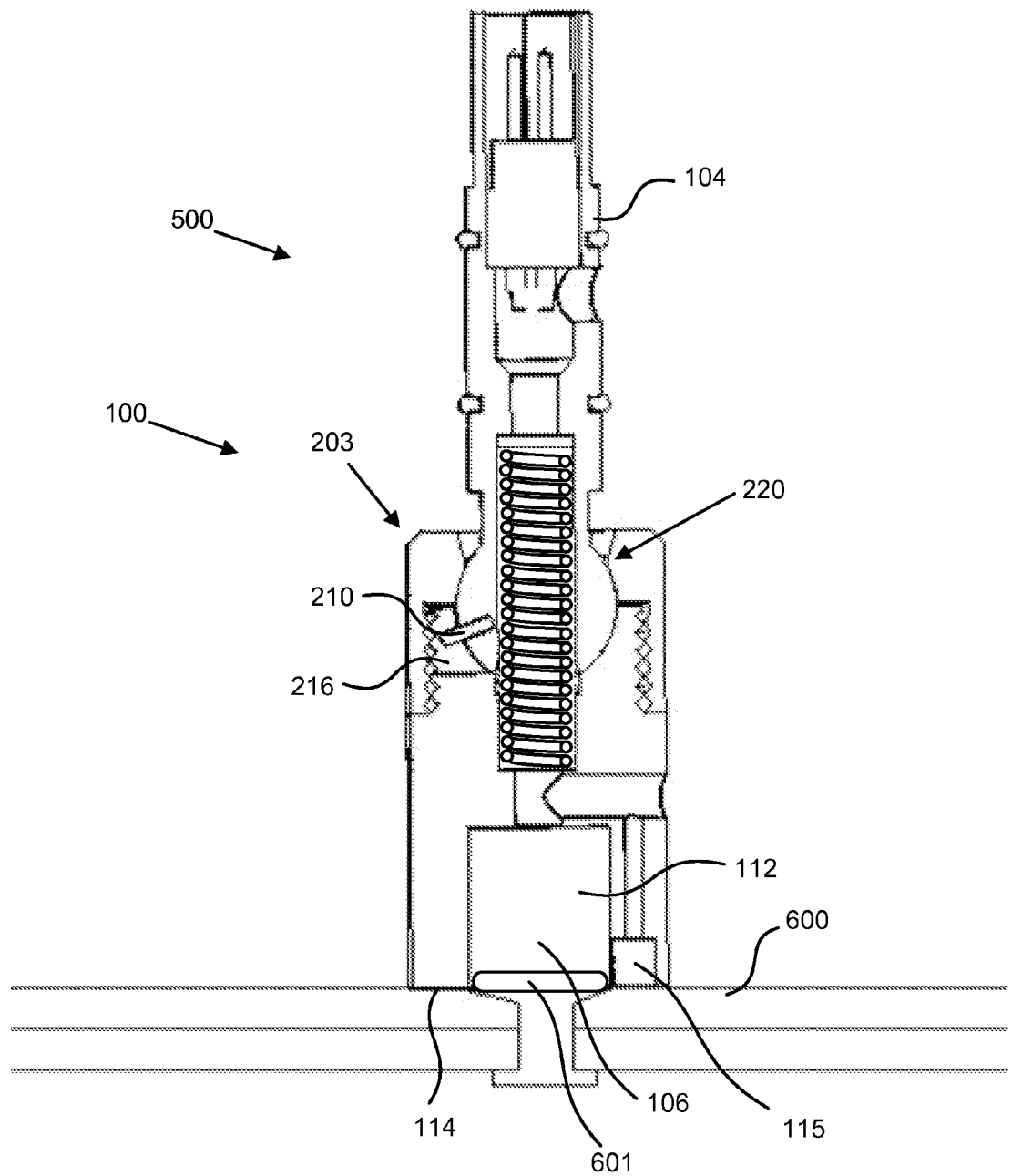
FIG. 6 is a cross-sectional view illustrating the apparatus of FIG. 4 with the feature engaging element of the rotating member in engagement with a feature on a scanned structure.

As shown in FIG. 6, the apparatus 100 is positioned on a scanned surface 600. As discussed above, in certain embodiments, the feature engaging element 106 includes a fastener receiving cavity 112. The fastener receiving cavity 112 is shown receiving a head of a rivet 601 positioned on the scanned surface 600. In other embodiments, the feature engaging element 106 may be adapted to receive rivets of a different size, bolts, screws, nuts, or any other type of fastener known in the art.

In certain embodiments, a driving tool such as a drill or other rotationally driving device rotates the shaft 104 causing the rotating member 102 to also rotate due to the engagement between the third coupling element 210 and the fourth coupling element 216 as described above. The rotation of the rotating member 102 causes the sensor module 115 to rotate around the rivet 601. This allows the sensing surface to scan the scanned surface 600 around the rivet 601 without scanning the rivet 601. With the head of the rivet 601 positioned within the fastener receiving cavity 112 the sensing surface 114 remains parallel with the scanned surface 600 and allows the sensing surface 114 to be positioned closer to the scanned surface 600 than would otherwise be possible. Additionally, the ball-and-socket joint 220 and the pin-and-slot as described above maintain parallel alignment of the sensing surface with the scanned surface regardless of the angle of the shaft 104 relative to the scanned surface, as well as co-rotation of the rotating member 102 and the shaft. This allows a user to more easily maintain the sensing surface 114 parallel to a scanned surface 600 because the user is not required to hold the user engaging portion 500 such that the shaft 104 is perpendicular to the scanned surface 600.

Figure 7:
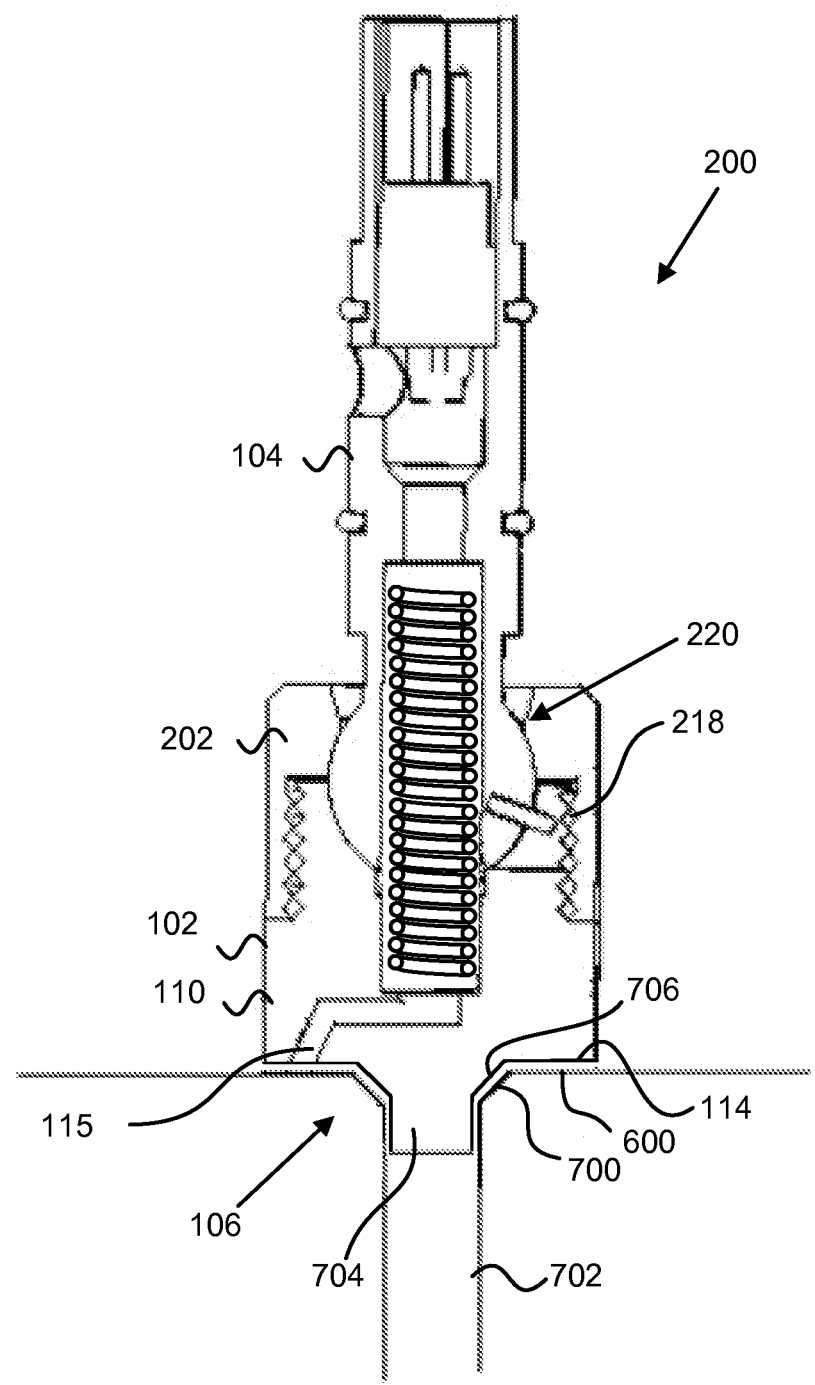
FIG. 7 is a cross-sectional view illustrating another embodiment of an apparatus for maintaining a sensing surface parallel to a scanned surface with a feature engaging element of a rotating member in engagement with a feature on a scanned structure.

According to another embodiment shown in FIG. 7, an apparatus 200 includes a shaft 104 and attachment end 202 that is substantially similar to the shaft 104 and the attachment end 202 of the rotating member 102 of apparatus 100. However, the sensing end 110 of rotating member 102 includes a feature engaging element 106 that is adapted to engage a chamfer 700 of a hole 702 in the scanned surface 600. In one embodiment, the feature engaging element includes a nub 704 that is adapted to fit within a hole 702 of a certain diameter. The feature engaging element 106 of apparatus 200 also includes a chamfer receiving face 706. The hole 702 may comprise a bolt hole, a rivet hole, a screw hole, or any other type of hole found on a scanned surface 600. As shown, the sensing surface 114 is positionable around a periphery of the feature engaging element 106 and the sensor module 115 is positioned on the sensing surface 114 such that the sensor module 115 scans the surface 600 surrounding the hole 702.

Figure 8:
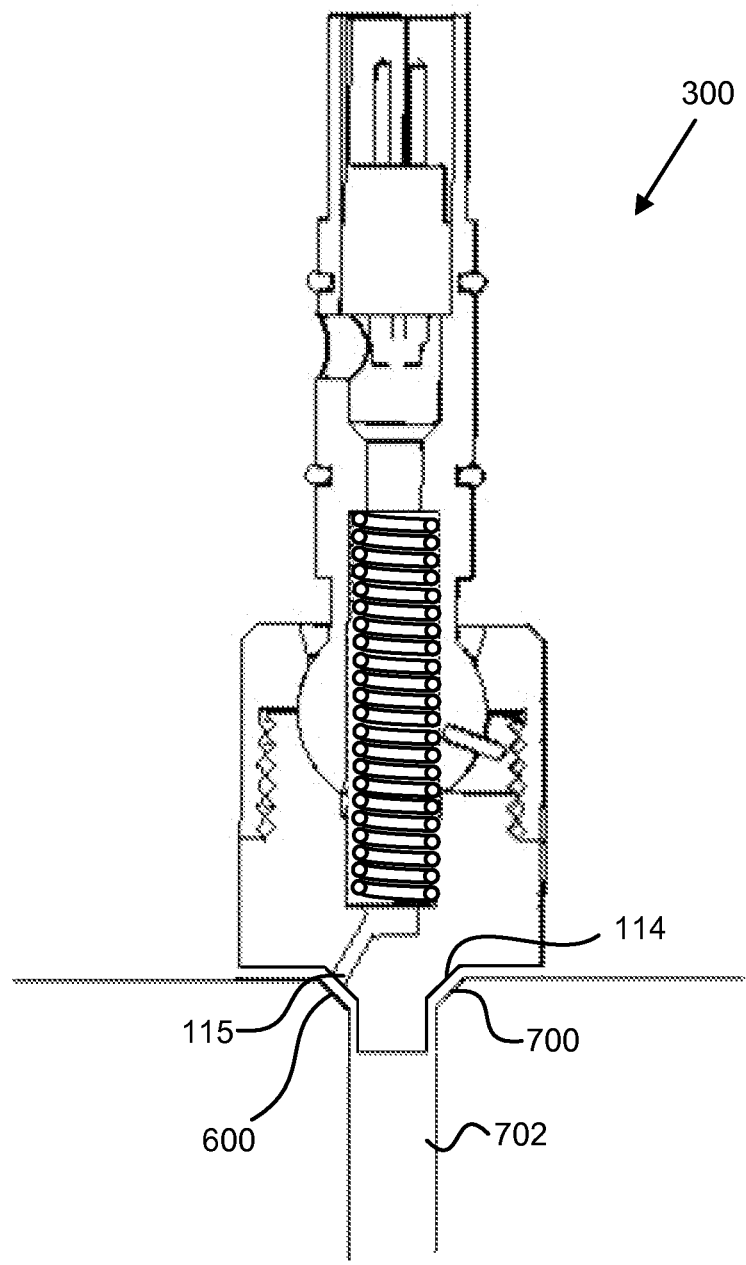
FIG. 8 is a cross-sectional view illustrating another embodiment of an apparatus for maintaining a sensing surface parallel to a scanned surface with the scanning surface scanning a chamfer on the scanned surface.

According to another embodiment shown in FIG. 8, an apparatus 300 the sensing surface 114 is disposed above (e.g., partially within) the chamfer 700 of the hole 702 such that the scanned surface 600 comprises the chamfer 700. In such an embodiment, the sensor module 115 may be positioned on the sensing surface 114 at an angle that is substantially parallel to the angle of the chamfer 700 of the hole 702. As the rotating member 102 is rotated, the sensor module 115 scans the chamfer 700 of the hole 702 for cracks or other imperfections.

FIGS. 7 and 8 both depict embodiments where the feature engaging element 106 is engaging a hole 702. This may be useful when scanning the surface of an aircraft that has had at least one rivet removed. It may be necessary to scan the chamfer 700 to ensure that the hole 702 is still suitable to use as a fastener hole. Moreover, in some embodiments, a plurality of feature engaging elements 106 may be provided and different feature engaging elements 106 may be attachable to the apparatus 100 based upon the feature on the scanned surface. The coupling portion 218 may allow different feature engaging elements 106 to be used by facilitating interchangeability between the sensing end 110 and the rotating member 102. The feature engaging element 106 may be changeable by detaching the sensing end 110 from the apparatus 100 using the coupling portion 218. In other embodiments, a separate apparatus having a different feature engaging element may be used for each type of feature on the scanned surface.

Figure 9:
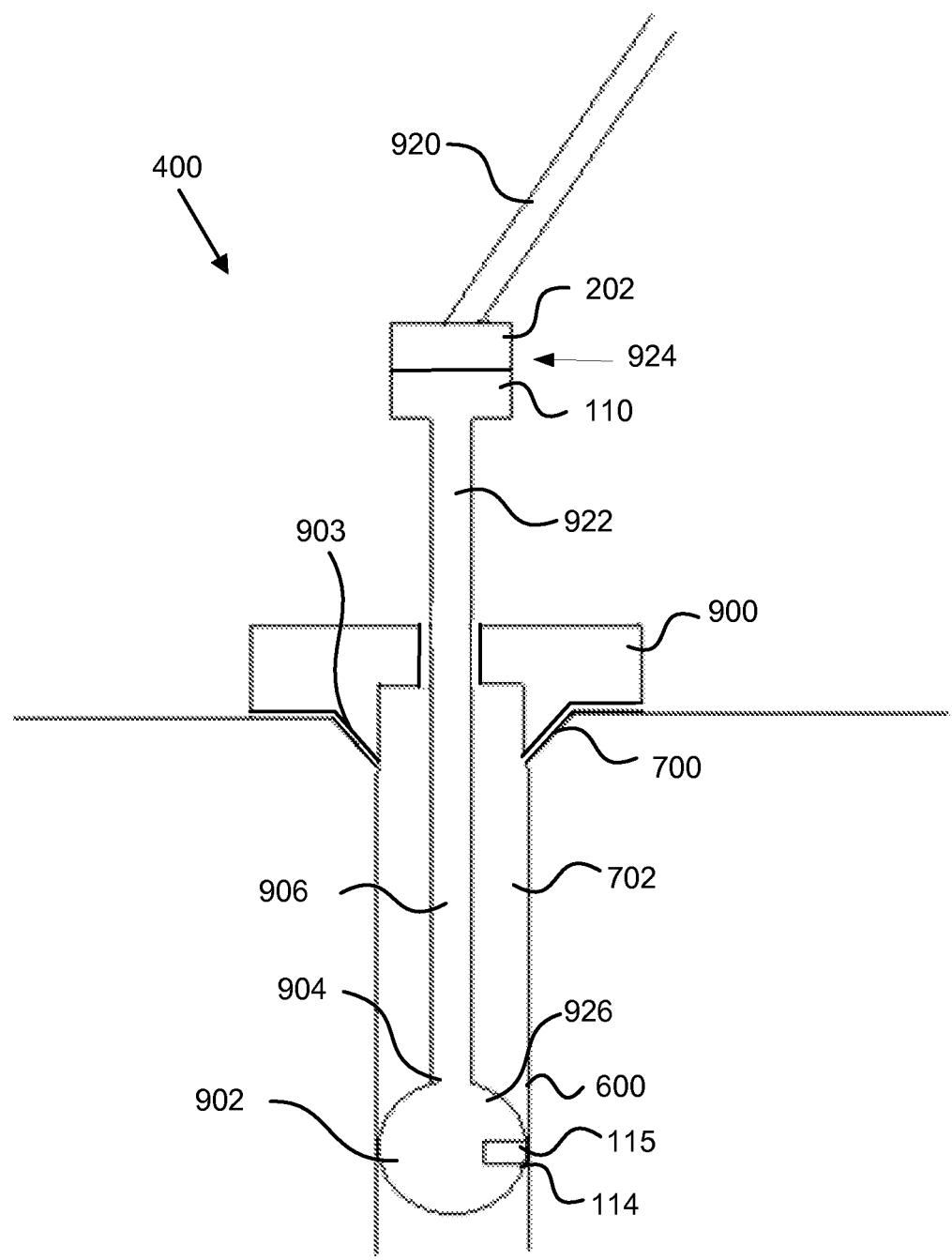
FIG. 9 is a cross-sectional view of another embodiment of an apparatus for maintaining a sensing surface parallel to a scanned surface with the scanning surface disposed in a hole in the scanned structure.

FIG. 9 depicts another embodiment of an apparatus 400 having a feature engaging element 106 that is adapted for scanning a surface 600 within a hole 702. The shaft 920 of the apparatus 400 may be coupled to a rotating member 922 with a ball-and-socket joint 924 substantially similar to the ball-and-socket joint 220 discussed above. Also, the coupling between the shaft 920 and the rotating member may include a pin-and-slot coupling to facilitate co-rotation of the shaft 920 and the rotating member 922 as discussed above.

The feature engaging element 926 of apparatus 400 may include a spherical element 902 positioned on an end 904 of an elongated section 906 of the rotating member 922. The spherical element 902 includes a sensing surface 114 having a sensor module 115. The sensing surface 114 is held parallel to a scanned surface 600 within a hole 702 when the elongated section 906 is positioned within the hole 702. In one embodiment, the spherical element 902 may be specifically sized such that the diameter of the spherical element is slightly less than the diameter of the hole 702. In such an embodiment, the spherical element 902 may freely travel down the hole, but also maintain the sensing surface 114 close to the scanned surface 600. One of skill in the art will recognize that the diameter of the spherical element 902 may be increased or decreased to fit within a specific hole 702.

The apparatus 400 may also include an aligning element 900 as part of the apparatus or a corresponding system that includes the apparatus. The aligning element 900 may provide additional support to the rotating member 922 as it is being lowered into the hole 702. In certain embodiments the aligning element 900 may include a chamfered edge 903 that is adapted to engage the chamfer 700 of the hole 702. In one embodiment, a plurality of different aligning elements 900 may be provided with each aligning element 900 adapted to fit a hole 702 with a specific size and/or shape.

Figure 10:
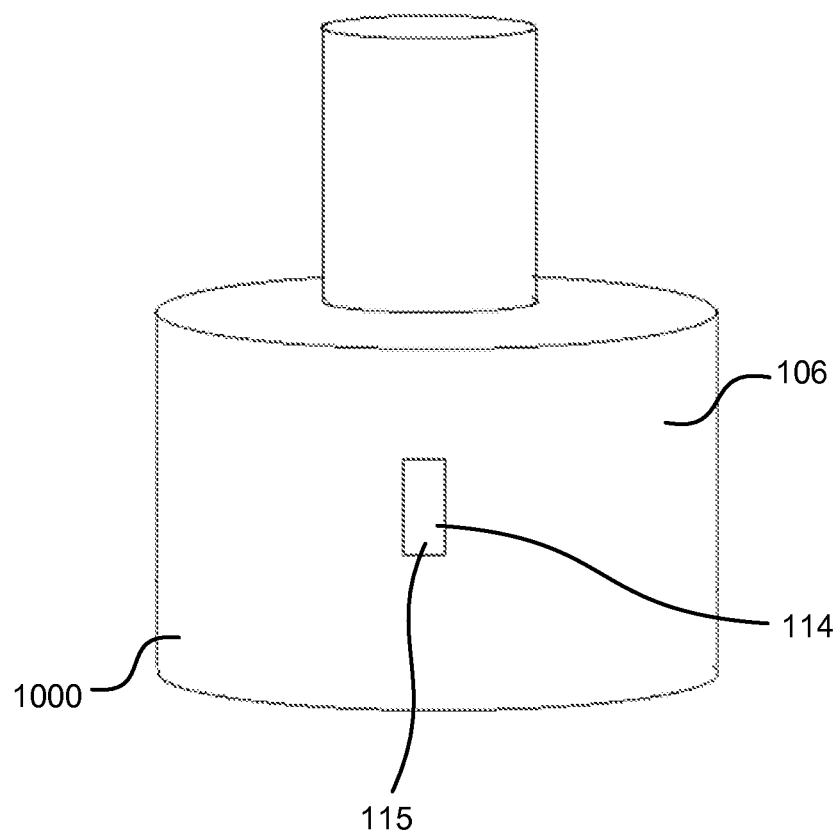
FIG. 10 is a perspective view illustrating one embodiment of a feature engaging element of an apparatus for maintaining a sensing surface parallel to a scanned surface.

FIG. 10 depicts an embodiment of a feature engaging element 106 that may be coupled to the elongated section 906 of the rotating member 102 in place of the spherical element 902 depicted in FIG. 9. In one embodiment the feature engaging element 106 is a cylinder 1000 having the same diameter as a hole, such as the hole 702. In certain embodiments the diameter of the cylinder 1000 causes the cylinder to self align with the scanned surface of the hole 702. The feature engaging element 106 includes a sensing surface 114 having a sensor module 115. When inserting the feature engaging element 106 into the hole 702, the cylinder 1000 aligns the feature engaging element 106 with the scanned surface of the hole 702 such that the sensing surface 114 will remain parallel to the scanned surface 600 of the interior walls of the hole 702.

Figure 11:
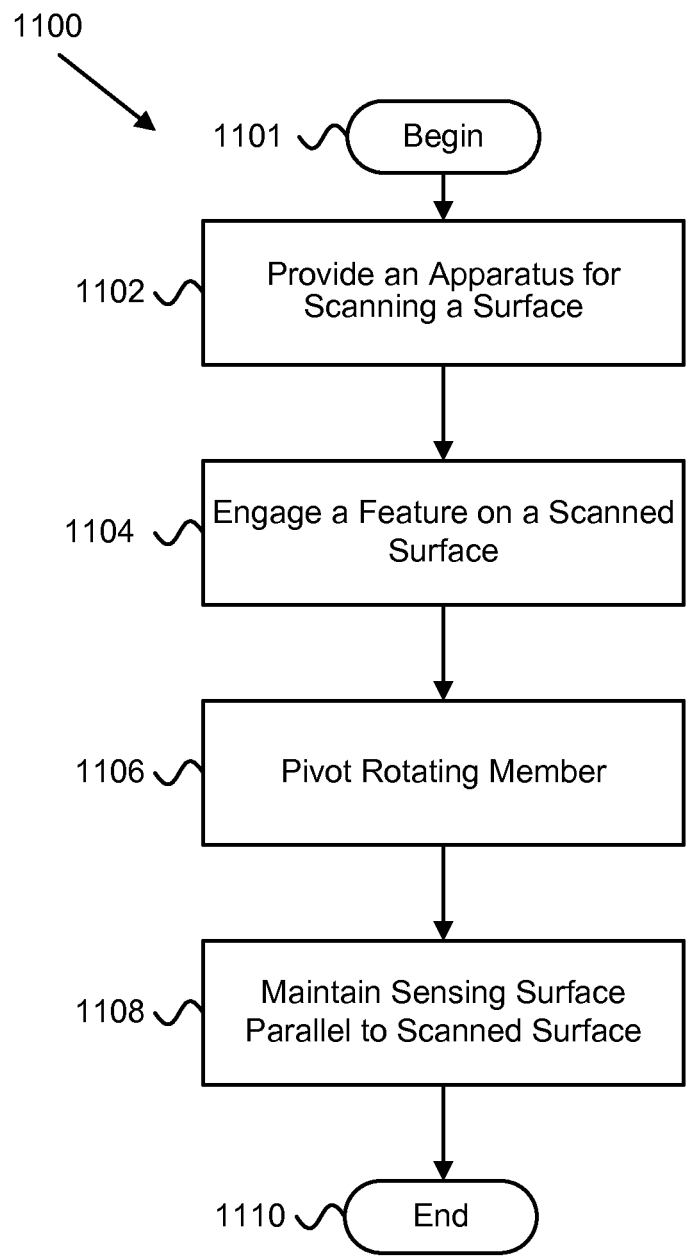
FIG. 11 is a flow chart depicting an embodiment of a method for scanning a surface.

FIG. 11 depicts one embodiment of a method 1100 for scanning a surface. In certain embodiments, the method 1100 utilizes an apparatus to induce a magnetic field into a surface and to sense for a reaction to that magnetic field. In one embodiment the apparatus may be substantially similar to one or more of apparatuses 100, 200, 300, and 400 discussed above. The method 1100 begins 1101 and an apparatus for scanning a surface such as apparatus 100 is provided 1102. In certain embodiments the apparatus 100 includes a shaft 104 and a rotating member 102 having a feature engaging element 106.

According to the method 1100, the feature engaging element 106 is engaged 1104 with a feature disposed on a scanned surface, such as scanned surface 600 described above. The feature engaging element 106 may engage the feature on the scanned surface to position a sensing surface 114 parallel to the scanned surface 600. In certain embodiments, the feature engaging element 106 may engage 1104 a rivet 601, a bolt, a screw, or any other fastener in a fastener receiving cavity 112. In other embodiments, the feature engaging element 106 may engage 1104 a hole, such as a fastener hole 702, or a chamfer 700 of a fastener hole 702.

A magnetic field is induced in the scanned surface 600. In some embodiments, this may comprise inducing eddy currents in the scanned surface 600 by passing an electrical current from a coil or other electrical current carrying element over the scanned surface 600. A reaction to the induced magnetic field is sensed using a sensing module 115. In certain embodiments, different reactions to the induced magnetic field may contain information about whether the scanned surface 600 comprises weaknesses or abnormalities. For example, in one embodiment a variation in an eddy current may indicate a crack or other weakness in the scanned surface 600. In certain embodiments the sensed eddy currents may provide feedback to a processing unit. The processing unit may interpret the feedback. In one embodiment the interpreted feedback may then be displayed by a display unit such as an LCD terminal or other display device known in the art. In one embodiment the interpreted feedback may be displayed as a two dimensional or three dimensional representation of the scanned surface 600 or structure.

The method 110 further includes pivoting 1106 the rotating member to any three-dimensional angle with respect to the shaft 104. In some embodiments, this may be accomplished by the apparatus 100 comprising a ball-and-socket joint 220. By pivoting 1106 the rotating member 102 to any three-dimensional angle with respect to the shaft 104, the sensing surface 114 may be maintained 1108 parallel to the scanned surface 600 irrespective of the orientation of the shaft 104 with respect to the scanned surface 600. In certain embodiments, this may allows a user to scan a surface while the shaft 104 is positioned at an angle other than a perpendicular angle with respect to the scanned surface 600. This may be useful in a situation where the scanned surface 600 is positioned at an angle that is difficult to scan or when the scanned surface 600 is in a position that is difficult to reach.

Figure 12:
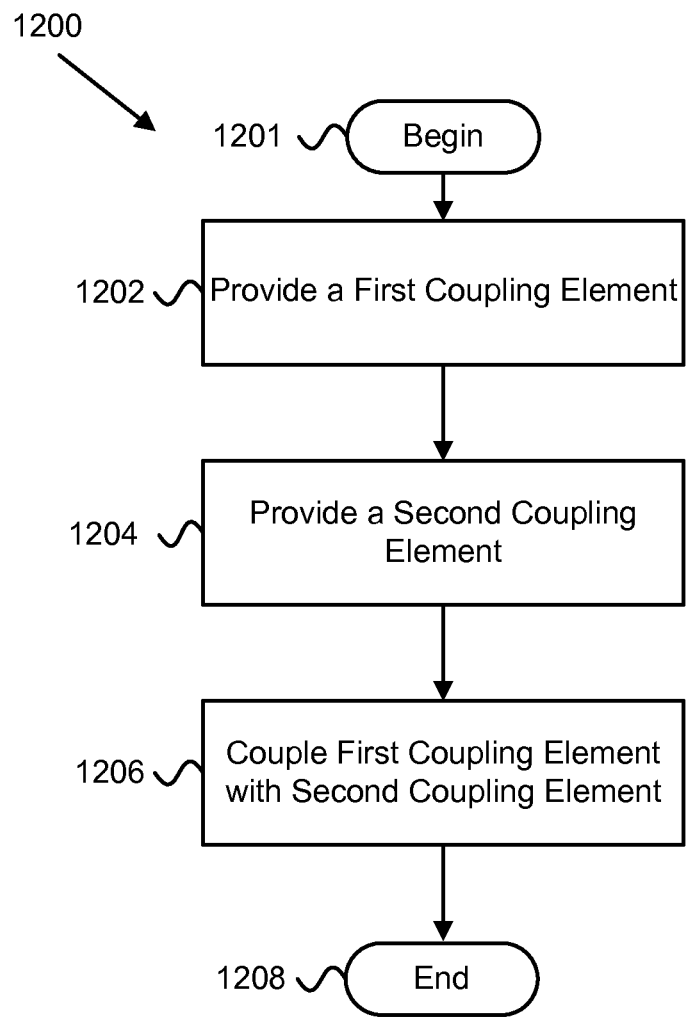
FIG. 12 is a flow chart depicting an embodiment of another method for scanning a surface.

FIG. 12 depicts another embodiment of a method 1200 for scanning a surface. In certain embodiments, the method 1200 may be used with method 1100 of FIG. 11. The method 1200 begins 1201 and a first coupling element 204 is provided 1202. In certain embodiments, the first coupling element 204 is coupled to the shaft 104. A second coupling element 203 is also provided 1204. The second coupling element 203 may be coupled to the rotating member 102.

In one embodiment the first coupling element 204 is a ball 208 and the second coupling element 203 is a socket 205 such that a combination of the first coupling element 204 and the second coupling element 203 forms a ball-and-socket joint 220. One of skill in the art will recognize that the position of the ball 208 and the socket 205 may be reversed. That is, in one embodiment the ball 208 may be coupled to the rotating member 102 and the socket 205 may be coupled to the shaft 104. The first coupling element 204 is coupled 1206 to the second coupling element 208. After coupling 1206 the first and second coupling elements, according to the ball-and-socket embodiments above, the ball-and-socket joint 220 created by the coupling between the ball 208 and the socket 205 allows the rotating member 102 to pivot at any three-dimensional angle with respect to the shaft to orient the sensing surface 114 parallel to the scanned surface 600.

Figure 13:
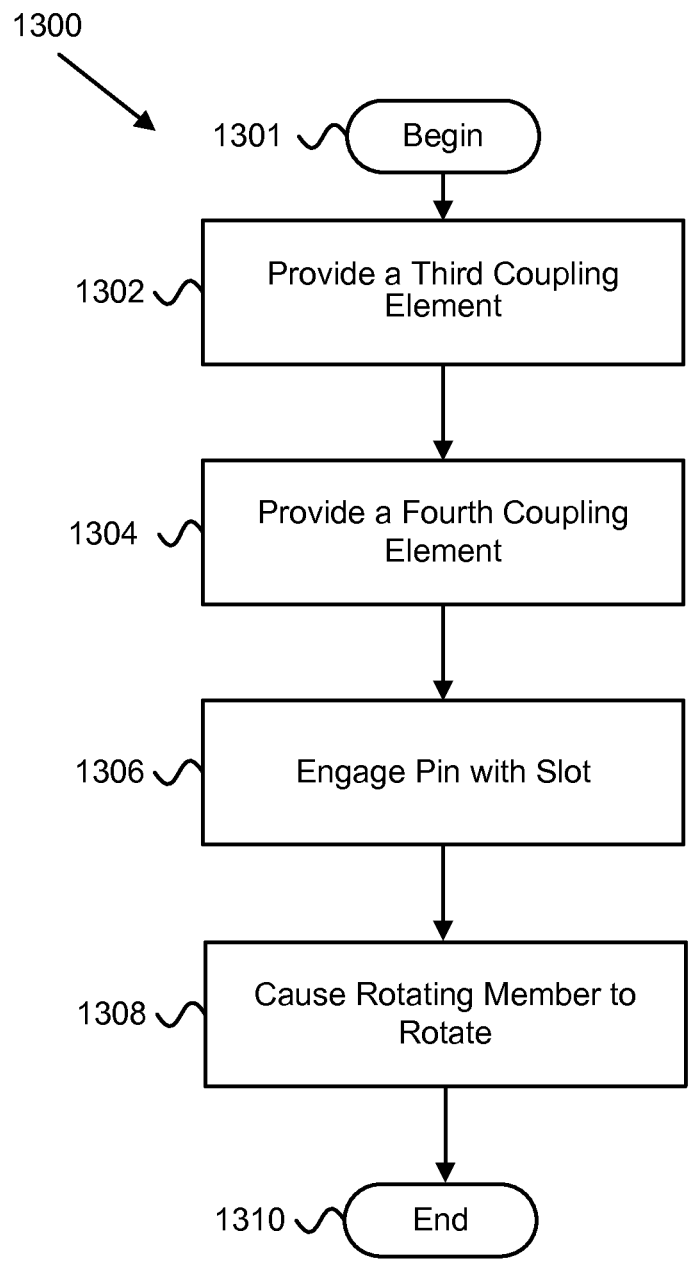
FIG. 13 is a flow chart depicting another embodiment of a method for scanning a surface.

FIG. 13 depicts another embodiment of a method 1300 for scanning a surface. In certain embodiments the method 1300 may be used with method 1100 and/or the method 1200. The method 1300 begins 1301 and a third coupling element 210 is provided 1302. In certain embodiments, the third coupling element 210 is coupled to the shaft 104. In one embodiment, the third coupling element 210 is disposed on the ball 208 which is in turn coupled to the shaft 104. A fourth coupling element 216 is provided 1304. In one embodiment, the fourth coupling element 216 is coupled to the rotating member 102. In certain embodiments, the third coupling element 210 may include a pin or a slot, and the fourth coupling element 216 may comprise the other of the pin or the slot. The pin is engaged 1306 with the slot such that rotation of the shaft 104 causes 1308 the rotating member 102 to rotate.

As discussed above, in certain embodiments, the rotating member 102 and the shaft 104 are coupled by the first coupling element 204 and the second coupling element 203 in a manner that allows the rotating member 102 to be positioned in any three-dimensional position with respect to the shaft 104. As further discussed above, engagement between the third coupling element 210 and the fourth coupling element 216 allows for co-rotation of the shaft 104 and the rotating member 102. Co-rotation between the rotating member 102 and shaft 104 can be defined to mean that the shaft 104 and the rotating member 102 rotate at the same rate. However, it is recognized that in other embodiments, the coupling between the shaft 104 and the rotating member 102 may include gearing that causes the rotating member 102 to rotate at a different rate than the shaft 104.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An apparatus to maintain a sensing surface parallel to a scanned surface, the apparatus comprising:
   a shaft comprising a first coupling element;
   a rotating member comprising a second coupling element coupleable with the first coupling element, the rotating member having a feature engaging element, the feature engaging element being engageable with a feature on a scanned surface, and the rotating member comprising a sensing end;
   a magnetic-field-inducing element and a sensing surface in communication with the sensing end of the rotating member, the sensing surface adapted to scan a surface; and
   wherein the coupling between the first coupling element and the second coupling element is such that the rotating member is pivotable at any three-dimensional angle with respect to the shaft to orient the sensing surface parallel to the scanned surface.

2. The apparatus of claim 1, wherein the sensing surface is disposed on the feature engaging element.

3. The apparatus of claim 1, wherein the feature engaging element comprises a geometric shape adapted to align a central axis of the feature engaging element with a central axis of a hole when the feature engaging element is inserted into the hole.

4. The apparatus of claim 1, wherein the feature engaging element comprises a fastener receiving cavity that is adapted to receive a head of a fastener.

5. The apparatus of claim 1, wherein the apparatus further comprises an aligning element adapted to align a central longitudinal axis of a hole with a central longitudinal axis of the rotating member.

6. The apparatus of claim 1, wherein the feature engaging element comprises a feature engaging chamfer, the feature engaging chamfer being engagable with a surface chamfer disposed on the scanned surface.

7. The apparatus of claim 1, wherein the rotating member includes a coupling portion, the coupling portion removably coupling the sensing end of the rotating member to the shaft.

8. The apparatus of claim 7, further comprising a second sensing end, each sensing end having a feature engaging element engageable with a different feature on a scanned surface, wherein the coupling portion facilitates interchangability between the sensing end and the second sensing end.

9. The apparatus of claim 1, wherein the first coupling element comprises one of a ball and a socket and the second coupling element comprises the other of the ball and the socket.

10. The apparatus of claim 9, further comprising a third coupling element disposed on the shaft and a fourth coupling element disposed on the rotating member, wherein the third coupling element includes one of a pin and a slot, and the fourth coupling element includes the other of the pin and the slot, the pin engaging the slot to facilitate co-rotation of the shaft and the rotating member.

11. The apparatus of claim 1, wherein the apparatus comprises a biasing member having a first end and a second end, the first end of the biasing member engaging the rotating member and the second end of the biasing member engaging the shaft, the biasing member biasing the rotating member into a coaxial alignment with respect to the shaft.

12. An apparatus to maintain a sensor module parallel to a surface, the apparatus comprising:
   a shaft comprising a first coupling element;
   a rotating member comprising a second coupling element coupleable with the first coupling element, and the rotating member comprising a sensing end;
   a sensor module in communication with the sensing end; and
   wherein the first coupling element is coupled to the second coupling element to allow infinite three-dimensional movement of the rotating member with respect to the shaft such that the sensor module remains parallel to a scanned surface.

13. The apparatus of claim 12, wherein the sensing end of the rotating member comprises a feature-engaging element.

14. The apparatus of claim 12, wherein the sensor module comprises a sensing surface.

15. The apparatus of claim 12, wherein the sensor module comprises a magnetic-field-inducing element.

16. The apparatus of claim 12, wherein the first coupling element comprises one of a ball and a socket and the second coupling element comprises the other of the ball and the socket.

17. The apparatus of claim 16, further comprising a third coupling element and a fourth coupling element, wherein the third coupling element includes one of a pin and a slot, and the fourth coupling element includes the other of the pin and the slot, the pin engaging the slot to facilitate co-rotation of the shaft and the rotating member.

18. A method for scanning a surface, the method comprising:
   providing a scanner for scanning a surface, the scanner comprising a shaft and a rotating member having a feature engaging element;
   engaging a feature on a scanned surface with the feature engaging element;
   pivoting the rotating member to any three-dimensional angle with respect to the shaft; and
   maintaining a sensing surface parallel to the scanned surface irrespective of an orientation of the shaft with respect to the scanned surface.

19. The method of claim 18, wherein the method further comprises:
   providing a first coupling element coupled to the shaft;
   providing a second coupling element coupled to the rotating member; and
   coupling the first coupling element with the second coupling element such that the rotating member pivots at any three-dimensional angle with respect to the shaft to orient the sensing surface parallel to the scanned surface.

20. The method of claim 18, wherein the method comprises
   providing a third coupling element coupled to the shaft;
   providing a fourth coupling element coupled to the rotating member,
      wherein the third coupling element includes one of a pin and a slot, and the fourth coupling element includes the other of the pin and the slot;
   engaging the pin with the slot; and
   causing the rotating member to rotate by rotating the shaft.

* * * * *